(12) United States Patent
Roesicke et al.

(10) Patent No.: US 7,988,917 B2
(45) Date of Patent: Aug. 2, 2011

(54) ANALYTICAL TEST ELEMENT WITH WIRELESS DATA TRANSMISSION

(75) Inventors: Bernd Roesicke, Mannheim (DE); Manfred Seidenstricker, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1021 days.

(21) Appl. No.: 11/733,059

(22) Filed: Apr. 9, 2007

(65) Prior Publication Data

US 2007/0237678 A1   Oct. 11, 2007

Related U.S. Application Data

(63) Continuation of application No. PCT/EP2005/010806, filed on Oct. 7, 2005.

(30) Foreign Application Priority Data

Oct. 7, 2004   (DE) .................. 10 2004 048 864

(51) Int. Cl.
 *G01N 27/00* (2006.01)
 *G01N 35/00* (2006.01)
 *G01N 27/26* (2006.01)
 *G01N 31/22* (2006.01)

(52) U.S. Cl. .......... 422/82.01; 422/68.1; 422/403; 422/420; 436/44; 436/149; 436/150; 204/400; 205/775

(58) Field of Classification Search .............. None
See application file for complete search history.

(56) References Cited

U.S. PATENT DOCUMENTS

| 4,442,836 A | 4/1984 | Meinecke et al. |
| 5,053,199 A | 10/1991 | Keiser et al. |
| 5,372,133 A | 12/1994 | Hogen Esch |
| 5,554,166 A | 9/1996 | Lange et al. |
| 5,580,794 A | 12/1996 | Allen |
| 5,597,532 A | 1/1997 | Connolly |
| 5,855,801 A | 1/1999 | Lin et al. |
| 6,217,744 B1 | 4/2001 | Crosby |
| 6,579,498 B1 | 6/2003 | Eglise |
| 6,689,320 B1 | 2/2004 | Markart |
| 2006/0121625 A1 | 6/2006 | Clemens et al. |

FOREIGN PATENT DOCUMENTS

| DE | 10211900 A1 | 10/2003 |
| DE | 10322167 A1 | 12/2003 |
| DE | 10234602 A1 | 3/2004 |
| DE | 10237602 A1 | 3/2004 |

(Continued)

OTHER PUBLICATIONS

Black, Joseph et al., "Integrated sensor—telemetry system for in vivo glucose monitoring", Sensors and Actuators B 31, 1996, pp. 147-153.

(Continued)

*Primary Examiner* — Jill Warden
*Assistant Examiner* — Neil Turk
(74) *Attorney, Agent, or Firm* — Justin L. Sage; Roche Diagnostics Operations, Inc.

(57) ABSTRACT

The present invention concerns embodiments of a system for determining the concentration of an analyte in a body fluid which comprises an analytical test element and an instrument separate therefrom, wherein at least a part of the electrical components of the system are comprised of polymer electronics. Embodiments of the analytical test element comprise an area with reagent chemistry for the detection of an analyte and a transponder configured for wireless transmission of lot-specific data and/or measured values. The instrument has a reading module configured for wireless transmission of data, or data and energy, to the test element and an evaluation unit for evaluating the data or measured values received by the transponder.

6 Claims, 8 Drawing Sheets

FOREIGN PATENT DOCUMENTS

| | | |
|---|---|---|
| DE | 10253154 A1 | 5/2004 |
| EP | 0554955 A1 | 8/1993 |
| EP | 0565970 B1 | 10/1993 |
| EP | 1225448 A2 | 7/2002 |
| EP | 1342448 A1 | 9/2003 |
| JP | 6007324 A | 1/1994 |
| JP | 2003348774 A | 12/2003 |
| WO | 98/48695 A1 | 11/1998 |
| WO | 03/100942 A1 | 12/2003 |
| WO | 2004/044571 A1 | 5/2004 |
| WO | 2005/024375 A2 | 3/2005 |

OTHER PUBLICATIONS

Puers, Robert, "Linking sensors with telemetry: impact on the system design", Sensors and Actuators A 52, 1996, pp. 169-174.

Stikeman, Alexandra, "Polymer Memory—The plastic path to better data storage", Technology Review, Sep. 2002, p. 31.

Fix, W. et al., "Fast polymer integrated circuits", American Institute of Physics, Applied Physics Letters, vol. 81, No. 9, Aug. 26, 2002, pp. 1735-1737.

Kraft, Arno, "Organic Field-Effect Transistors—The Breakthrough at Last", Chemphyschem, 2001, 2, pp. 163-165.

Clemens, Wolfgang, et al., "From the Organic Transistor to the Plastic Chip", Physik Journal 2, 2003, Nr. 2, pp. 31-36.

Clemens, Wolfgang, "Polytronics: Chips from the roll", Fraunhofer Magazin 4, 2001, pp. 8-13 (XP-002257822).

Guo, Xin, et al., "Darkening of zirconia; a problem arising from oxygen sensors in practice", Sensors and Actuators B31, pp. 139-145 (1996).

Salehi, Ceeyavash, et al., "A Telemetry-Instrumentation System for Long-Term Implantable Glucose and Oxygen Sensors", Analytical Letters, 29(13), pp. 2289-2308 (1996).

ANALYTICAL TEST ELEMENT WITH WIRELESS DATA TRANSMISSION

REFERENCE TO RELATED APPLICATIONS

The present application is a continuation of PCT Patent Application No. PCT/EP2005/610806, filed Oct. 7, 2005 which claims priority to German Patent Application No. 102004048864.9, filed Oct. 7, 2004, which are hereby incorporated by reference in their entirety.

TECHNICAL FIELD

The present invention concerns a system for determining the concentration of an analyte in a body fluid. Furthermore, the present invention concerns a process for producing such a system.

BACKGROUND

In clinical diagnostics the examination of body fluids enables an early and reliable detection of pathological states as well as the targeted and well-founded monitoring of physical conditions. Nowadays individual analyses that are specifically directed towards one parameter often require a few microliters of blood and even down to less than one microliter. Blood is typically collected by piercing the skin of the person to be examined, e.g. the finger pad or the earlobe with the aid of a sterile sharp lancet. This method is especially suitable when the analysis of the blood sample can be carried out directly after blood collection.

Substrate-based spot-monitoring tests are well established for the chemical and biochemical analysis of body fluids in specialized laboratories for these analyses but in particular also for use outside permanent laboratories. Such substrate-based spot-monitoring tests based on a specifically developed dry chemistry can be carried out simply and in an uncomplicated manner even by laymen despite the often complex reactions involving sensitive reagents. The most prominent examples of substrate-based spot-monitoring tests are test strips for determining the amount and/or concentration of blood glucose in diabetics.

In the diagnostic tests that are used nowadays for detecting an analyte (e.g. blood glucose) in a body fluid (e.g. blood), the function of lancing to generate a skin opening and the concentration determination function are typically divided among several components, e.g. a lancing device for lancing and generating a drop of blood, and an analytical test element e.g. a test strip for receiving the drop of blood, passing the blood from the receiving site to the reaction area and determining an analyte, e.g. blood glucose.

Lancets and suitable devices for them which enable a relatively painless and reliable collection of blood are offered generally in the field of so-called "home-monitoring", i.e. where patient consumers themselves carry out simple analyses of blood and in this case especially for the periodic blood collection by diabetics that often has to be carried out several times daily to monitor the blood glucose concentration. Examples of lancets and lancing devices are the commercially available devices and lancets Glucolet® from Bayer AG and Soflclix® from Roche Diagnostics GmbH. Such lancets and devices are for example the subject matter of WO 98/48695, EP 0,565,970, U.S. Pat. No. 4,442,836 or U.S. Pat. No. 5,554,166, each incorporated herein by reference.

The self determination of blood glucose is nowadays a world-wide method in diabetes monitoring. Blood glucose instruments in the state of the art such as the AccuChek® Advantage (from Roche Diagnostics) consist of a measuring instrument into which a test element (test strip) is inserted. The test strip is for example brought into contact with a drop of blood which has been previously collected from the finger pad by means of a lancing device. On the test strip the blood is transported into the area in which the reagent chemistry is located. Here the analyte to be analyzed reacts with the reagent chemistry and generates a measurement signal, e.g. an electrical current impulse or a change in color. The measurement signal is evaluated by the measuring instrument and a timely blood glucose value is shown to the user on the display of the blood glucose instrument.

In order to rigorously monitor the blood glucose content it is necessary to regularly carry out glucose measurements for example several times daily. A new test strip which is provided in storage vials containing for example 50 strips is required for each measurement. In this regard it should be born in mind that the test strips can have a different quality and different properties depending on the strip lot which can influence the measured result. It is therefore often necessary to calibrate the glucose measuring instrument before inserting the measurement strip. These variations are typically due to unavoidable tolerances during test strip manufacture and/or the reagent chemistry. In order to compensate for this, a large number of samples of each production lot are measured and lot-specific calibration data are determined from these measurements. These data are delivered to the customer together with the test strips, but are not necessarily visible to the customer. The set of data consists of a lot number and values which describe a correction function.

In many known measurement systems, it is known to provide a number code on the storage container for the test strips which has to be entered by means of an appropriate input unit on the glucose measuring instrument in order to adjust the glucose measuring instrument to the test strips in this container. It is also known to provide a film foil in each test strip container. In that case, the transparent film foil contains a barcode which contains the coefficients of a polynomial of the nth order in binary code. In other known systems, such as in the case of the glucose measuring instruments Accu-Chek Compact® and Accu-Chek Comfort® from Roche Diagnostics GmbH, an electronic storage medium, a so-called ROM key, on which a complete set of the coefficients of a polynomial is stored (see U.S. Pat. No. 5,053,199), is enclosed with the test strips. This ROM key is inserted into the measuring instrument, the data are read from the storage medium by the measuring instrument and used for the correction calculation. Furthermore, U.S. Pat. No. 6,689,320 also describes an electronic data carrier which, however, is inserted into the measuring instrument in a so-called code carrier; in this case the data are transferred using a transponder.

A common feature of all aforementioned calibration methods is that the user has to carry out a large number of steps in order to calibrate the glucose measuring instrument to the test strip lot. There is a risk that errors may occur in the manual input or that one forgets to insert the ROM key or insert the film foil with the lot-specific code. Especially when the user is using several containers containing test strips, there is a risk that a calibration of the glucose measuring instrument to the current test strip lot may be forgotten. In order to avoid this risk, it is known to provide a lot-specific identification in the form of a bar code or magnetic strip on the test strips themselves in addition to the external data store which contains the calibration data. In any event, special care must be taken that despite the separate test strip and data carrier logistics, it is ensured that the correct correction values are enclosed with the test strips.

One method of avoiding the risk of confusion and error is to directly connect the entire calibration data with the test strip. The test strip for the Reflochek® from Roche Diagnostics GmbH for example has a bar code printed on, and a magnetic strip is glued onto the Reflotron® strip (Roche Diagnostics GmbH).

However, as the development progresses towards smaller and smaller test strips and at the same time more and more calibration data, the data capacity of such miniaturized bar code or magnetic strips reaches its limits.

Hence DE 102 37 602 describes a system for blood glucose measurement in which a data carrier with adequate capacity is present on the test strip itself in order to store all required data on the strip. The calibration unit in this blood glucose measuring system comprises a receiver unit which interacts with a transmitter unit on the test strip for the wireless transmission of a signal which reflects the quality and/or the properties of the test strip. This wireless and non-contacting transmission of calibration data means that the user does not have to carry out any additional steps for calibration of the instrument to the currently-used test strip. It is only necessary that the test strip is held near to the measuring instrument, which is the case, for example, when the strip is inserted into the measuring instrument. The receiver unit and the transmitter unit in this case fort a so-called transponder system.

R. Puers describes a transponder system which is used in orhthopaedic implants ("Linking Sensor Systems with Telemetry: Impact on the System Design", Sensors and Actuators (1996) 169-174).

J. Black et al. describe an implantable amperometric glucose sensor with an integrated telemetry unit as an example for transmission of analogue data ("Integrated Sensor-Telemetry System for in vio Glucose Monitoring", Sensor and Actuators (1996) 147-153).

A heart pacemaker is described in WO 031 00942 which receives its energy via a transponder from an extracorporeal battery unit. In return the heart pacemaker transmit its charge state to the outside.

U.S. Pat. No. 6,217,744 concerns a disposable test strip for blood glucose measurement which transmits its measurement data via a transponder to the information device where the blood sample itself serves as an electrolyte for the battery in the disposable.

In view of the foregoing, it is an object of the present invention to employ, in the context of a system for determining the concentration of an analyte in a bodily fluid, a transponder system that comprises a reading/receiving system, which corresponds to the aforementioned receiver unit in the measuring instrument, and the actual transponder, which corresponds to the aforementioned transmitter unit on the test strip. The energy required for the measurement can be provided to the test strip by the receiving system, i.e. the test strip does not have its own power supply. In one useful embodiment, the transmitter unit on the test strip transmits the stored calibration data as well as the measured signals of the current measurement to the measuring instrument.

Transponders are typically provided with microprocessors in silicon technology. Although the manufacturing costs for silicon chips have decreased considerably in recent years due to miniaturization, integration and optimization of the manufacturing processes, they are nevertheless still at such a high level that they would disproportionately raise the cost of a measurement if each individual test strip that is discarded after a single measurement would be equipped with such a silicon chip. To overcome this and satisfy the objects of the present invention, a more practical embodiment of a transponder system is disclosed herein.

SUMMARY OF THE EMBODIMENTS OF THE PRESENT INVENTION

The present invention describes a system which ensures that the correct calibration data are used for each analyte measurement without the risk of a mix-up. Moreover, the quality of the measured analyte values is improved by increasing the accuracy of the measurements by an improved measuring setup.

Security against a mix-up of the calibration is ensured by storing the lot-specific identification and the calibration data on each test strip. The above-mentioned transponder system technology is used to store the required amount of data and transmit it to the measuring instrument. In this regard, in one embodiment the electrical components on the analytical test element at least partly comprise polymer electronics.

According to the present invention, it was found that the application of transponder technology utilizing polymer electronics in systems for determining an analyte in a body fluid is particularly useful.

Polymer electronics is based on the premise that certain polymers (e.g. pentacene, polythiophene) have semi-conducting properties and thus can be used to make electronic circuits. Thus for example a binary data memory can be directly incorporated into the substrate of a test strip ("Vom organischen Transistor zum Plastik-Chip", Physik Journal 2 (2003) No. 2, p. 31-36). In this case, spatially discrete zones either of a lower or of a higher conductivity extending through the conductive polymer substrate are generated by the pointwise application of electrical fields depending on the polarity. The conductive state is retained after removing the electrical field. The state can be restored again by reversing the polarity of the electrical field. Hence this enables writing/reading processes and the storage of information such as lot numbers and corrections curves (calibration data) directly on the substrate of the test strip. The punctiform fields are for example formed by applying a voltage to column and line leads by means of a decoder circuit preferably made of semi-conducting polymers ("Polymer Memory", Technology Review (September 2003), p 31). In addition it is also possible to use conductive polymers to form further components which are necessary for electrical transponder functions (transistors, diodes, resistors, capacitors coils, leads, contacts) directly on the test strip ("Fast Polymer Integrated Circuits", American Institute of Physics (2002), p. 1735-1737).

Terms such as integrated plastic circuits (IPC), organic electronics, polytronics, electronic plastic, organic semi-conductors or conductive polymers are often used synonymously for this technology of polymer electronics. These polymers can for example be applied by simple printing techniques such as offset, tamp-on, screen printing or technologies similar to laser or ink-jet printing, e.g. using polymers in solution (so-called electronic ink). This technology is especially advantageous for applications on fat carrier foils which is typically the case for analytical test elements. Moreover, since printing and laminating techniques are already routinely used to manufacture analytical test elements, polymer electronics can be readily integrated into the existing production process. For example DE 102 53 154 describes how the electronics for a complete blood glucose measuring system in a credit card format consisting of a measuring unit and biosensor are applied in polymer electronics in a single printing process.

Test strips are typically produced in so-called continuous processes (roll-to-roll processes). The rolls are subsequently cut into test strips and filled into packaging units (vials, magazines). At the same time samples are taken from each production lot and validated. The deviations from the target values are converted into a data set by means of an algorithm and stored on a data carrier. The packaged test strips are brought together with the data carriers and delivered in a confectioned form.

In embodiments of the present invention, the use of transponder technology combined with polymer electronics enables a transponder to be applied to the analytical test element in a simple process step that can be easily integrated into a continuous production process. Furthermore, a transponder comprising polymer electronics can be manufactured extremely cost-effectively which is of major importance especially for single measuring strips which are discarded after single use. The present invention enables the analytical test elements to be provided with a lot-specific identification during the manufacturing process and to transfer the calibration data in a non-contacting manner to the separated and packaged test elements. This means that it is not necessary to store the calibration data on a separate data carrier in order to ensure that the test strips have been correctly packaged with the appropriate data carrier. The transponder system can be used to write data onto the analytical test element as well as to read data stored on the test element or generated during the measurement.

Thus, for example the lot numbers of the test elements filled in a container can be firstly read by a special reading unit in the production process. The calibration data for the respective lot numbers are stored in the reading unit. The reading unit then selects the matching calibration data and transfers them to the test elements. In order to check whether the calibration data have been correctly transmitted, it is possible for the stored data to be finally read. In an additional embodiment of a method in this regard the number of response signals can for example be used to check whether the correct number of test strips have been packaged and whether all test strips have stored the correct data set. It is also possible to also provide the analytical test elements with an unequivocal identification number in addition to the lot number in order to thus be able to write and read each individual test strip. In this manner the method according to the present invention ensures that the correct calibration data are used for each measurement and a mix-up is prevented during the packaging, during manufacture, and when used by the customers.

The lot-specific calibration data can for example be a complete calibration curve or certain supporting points are defined to which a specified curve is fitted that is for example stored in the instrument. Furthermore, the calibration curve can be shown as a polynomial function in which case for example either the entire function or the variables of the polynomial serve as lot-specific calibration data while the polynomial function is stored in the instrument. The curve or the polynomial function can also be stored on a ROM key which accompanies the instrument and is inserted by the customer into the instrument, instead of the function being stored directly in the instrument. If the curve has to be fitted at a later time, for example when a new design generation of test strips with slightly changed measuring properties is launched, the instrument can be adapted to them by simply exchanging the ROM key.

In one embodiment, the lot-specific calibration data are stored on the analytical test element or on its packaging and the calibration curve is stored in the instrument for example in the form of a polynomial function. Alternatively, several calibration curves, for example with different identification numbers, can be stored on a ROM key and the identification number of the calibration curve which matches this lot is stored on the test strip.

Another feature of the combination according to the present invention of transponder technology and polymer electronics is the ability to improve the measuring technology on the analytical test element. The measurement of electrochemical parameters is essentially based on electrolytic processes or electron mobilities in liquid phases. If several electrochemical sensor systems are used in a common liquid circuit, they are inevitably connected electrolytically or in an undefined electrical manner by common electrical circuits such as the power supply and ground leads or by parasitic conducting mechanisms. Electrochemical measurements are typically direct current or low frequency processes, i.e. they are essentially galvanic (i.e. conductive) mechanisms which lead to background currents which can affect the accuracy of the measurements as well as the chemical reaction itself. Elaborate isolation amplifiers are often used nowadays to avoid these problems. These separate the electro-chemical measurement systems to such an extent that the only connection is via the unavoidable liquid electrochemical path. As a result of this "single connection", no superimposed electric circuit is present through which the parasitic electric current can flow. Transformer isolation amplifiers that are commonly used nowadays are typically expensive since small direct parameters (current, voltage) have to be converted into alternating parameters in a complicated manner. An additional power source that is galvanically separated from the remaining system would have to be provided for such an analytical test element. These are typically batteries or power supply units separated by transformers which have a relatively large installation size. There are also optical isolation systems as an alternative to electrical isolation amplifier systems. In this case the measurements obtained as electrical direct parameters are transmitted with light barriers according to the opto-electrical principle. However, in the case of optical isolation systems the supply energy can only be transmitted to a limited extent and with a relatively poor efficiency.

It was found that instead of isolation amplifiers, transponders in particular are also suitable for galvanically separating electrical systems. The combination according to the present invention of transponder technology and polymer electronics enables an analytical test element to be provided cost-effectively and manufactured in large numbers in which parasitic creepage currents are avoided by galvanic decoupling. In particular the required transmission of small measurements at high potential differences is possible with transponders without potential carry over. In this case the energy is transmitted in a wireless and non-contacting manner from the reading module located in the instrument to the transmitting module located on the analytical test element by a transformer in the form of an alternating voltage according to the induction principle. Especially the flat structures of polymer electronics applied to foils enable a good linear magnetic transmission of the signals via the transformer coils. The energy starts the measurement on the analytical test element. The electrical measurement signal is firstly obtained as a D.C. parameter (current or voltage), subsequently converted into an A.C. parameter, and then transmitted to the instrument by induction, for example by magnetic field coupling in a near field by modulating the signal onto a carrier frequency. Embodiments of the system according to the present invention thus enables a non contacting, bidirectional data transmission.

It should be understood that any reference to "transmitting", "receiving" or "reading" with respect to a transponder module is not an exclusive indication of the directionality of the communication with respect to that module, but rather only a primary indication of such directionality. Any transponder module, as will be seen throughout this disclosure, conceivably could transmit as well as receive (or receive as well as transmit) a wireless signal to suit the particular purpose, use or advantages of the present invention.

Transmission coils applied using polymer electronics can be extremely closely adjacent to one another or on top of one another at a distance of about 0.1 mm. This enables the use of small coil dimensions which is particularly advantageously for the miniaturization of the analytical test elements. Polymer electronic technology not only allows planar structures to be applied but also three-dimensional structures such as that of a field effect transistor can also be applied by using several layers ("Organic Field-Effect Transistors—The Breakthrough At Last", Chemphyschem (2001, 2002), 163-165).

Embodiments of the present invention concern a system for determining the concentration of an analyte in a body fluid which comprises an analytical test element and an instrument that is separate (e.g. remote) therefrom wherein at least a part of the electrical components of the analytical test element comprises polymer electronics. An area containing reagent chemistry for detecting the analyte is located on the analytical test element and the instrument has an evaluation unit for evaluating data.

One embodiment of the present invention concerns a system described above, wherein a transmitting module is located on the analytical test element and configured for wireless transmission of data. The instrument also has a reading module configured for wireless transmission of data. The transmitting module and reading module employ the transponder technology described above.

The system according to some embodiments comprises the components that are necessary to determine the concentration of an analyte in a body fluid. The system at least comprises an analytical test element with reagent chemistry and an instrument with an evaluation unit. In particular the system can additionally comprise for example a lancing device and a display unit, where these two components can be integrated into the test element or instrument or be independent units.

Analyte is understood to mean a component of the body fluid which reacts with the reagent chemistry in the detection area such that the reaction can be measured in a measuring arrangement above a certain amount of analyte. One embodiment is to use blood as the sample liquid and to detect blood glucose as an analyte in the detection area and thus to determine the concentration of blood glucose.

It is possible to also use interstitial fluid and other endogenous fluids as body fluids in addition to blood. It is also possible to detect not only one analyte, e.g. blood glucose, but also several analytes, e.g. HbA1C, and to detect them in a body fluid, e.g. blood, as well as in a mixture of several body fluids, e.g. blood plus interstitial fluid.

An analytical test element is understood as any form of substrate-based spot-monitoring tests for diagnostics especially spot-monitoring tests in a strip form, so-called test strips, in this case especially for determining the blood glucose content in diabetics.

The term "Instrument" refers in this disclosure to the part of the system which receives the measurement signals which are generated in the analytical test element and evaluates them in the evaluation unit. The instrument can also comprise a holder in which an analytical test element or a package for one or more test elements, e.g. a cartridge or a magazine, is positioned. Furthermore, a display unit e.g. a LCD display can also be integrated into the instrument. The instrument is typically a battery-driven hand-held device.

Currently, the electric leads and contacts on the analytical test element are typically made of gold or similar inert metals provided in a structured manner, such as by laser ablation.

According to the present invention, polymer electronics can be used instead of metal for the conductor paths and contacts. Thus for example a test strip that is currently available on the market having gold contacts and a data carrier (e.g. a magnetic strip or bar code) far identifying the strip can be replaced by an analytical test element in which the electrical leads and contacts are formed by polymer electronic conductor paths and contacts. In one embodiment, the strip identification is stored in a polymer electronic memory. In other embodiments, a polymer electronic transponder for writing and reading the memory can also located on the analytical test element. Of course it is also possible to relocate only the gold contacts or only the data carrier by polymer electronics, such as the polymer electronic transponder.

In certain embodiments, the polymer electronics can be used on the test element as well as in the instrument. In other embodiments, some or all electrical components on the analytical test element comprise polymer electronics and conventional technology is used for other electronics in the instrument.

The transmitter module on the analytical test element serves as a transponder on which data such as for example identification data (e.g. lot number, strip type, optionally serial number), expiry date and lot-specific calibration data are stored during test element production. It is also possible to store additional data after test element production such as updated notes for customers, logistic data, information for the retail trade, e.g. the pharmacy, or others. As soon as the test strip is inserted into the instrument, identification data can be transmitted to the instrument to check for example whether a test strip that is suitable for the instrument has been inserted or whether the expiry date has expired. Where appropriate it is also possible to display notes or information for the customer which had been stored in advance on the analytical test element. Subsequently, the measurement signals generated during the measurement of the concentration of the sought-after analyte can be transferred from the test strip to the instrument.

The reading module converts the signals received from the transmitter module and passes them onto the evaluation unit in which they are evaluated. The result, for example the concentration of blood glucose is shown to the user in the display unit e.g. a LCD display. The display unit is typically integrated into the instrumental but it is also possible for the display to be an independent unit. For example the test element can be designed as an implant or partial implant, the instrument together with the reading module is accordingly worn over the test element directly on the skin or over the clothing, and the display unit can be a type of wristwatch which is attached to the wrist. A transponder system could also used to transmit the data from the evaluation unit to the display unit. In addition it is of course also possible in this manner to actuate further modules such as an insulin pump or an electronic diabetic diary.

The transponder system according to some embodiments of the present invention uses frequencies in the region of 125 kHz with a range in the body of about 10 to 20 cm such as those used in implants to identify animals for wireless transmission from an implanted test element to an extracorporeal reading module. Frequencies in the region of 13.56 MHz which can cover a distance of approximately 1 m in air are for example used for transmission from a reading module to an independent display unit or other external system components, e.g. an insulin pump, or a data management system such as an electronic diary. If, in addition, it is intended to transmit data over large distances, e.g. to secondary external instruments such as a PC for data management, it is possible to use frequencies in the range of 800 to 2000 MHz (UHF range) to cover distances of up to approximately 4 m.

The measured values which are generated during the measurement of the concentration of the sought-after analyte are transmitted in a wireless and non-contacting manner from the measuring module to the transmitting module. In this connection wireless and non-contacting should only be understood as the signal transmission and optionally the transmission of energy. The electrical components on the analytical test element or in the measuring instrument are of course wired with electrical circuits and of course it is also possible that the analytical test element touches the instrument especially when the test element is inserted into the instrument. However, wireless and non-contacting data transmission has certain advantages over contact-linked data or energy transmission; thus, depending on the dimensions of the transponder coils the positioning tolerance of the analytical test element relative to the measuring instrument is considerably larger. Moreover, the transmission resistance of electrical contacts is very critical for high-impedance, low-current signals such as those that are typical for the present application. Ideally, one tries to design the contacts to be as reliable as possible e.g. by using inert materials such as gold and by giving the counter-contacts a pointed shape such that they dig into the flat contact surfaces in order to remove any deposits that may be present. Nevertheless an insulating layer or a short-circuit or leakage current may be formed between the contacts that are in close proximity to one another due to hand perspiration during the handling of the test element or a contact may be interrupted by scratches or a leakage current to a neighbouring contact may occur.

These contact problems are solved by the transponder system according to embodiments of the present invention. In one embodiment at least the sensitive measurement data are transmitted in a wireless manner, such as when the energy for conducting the measurement on the test element continues to be available via the electrical contacts or when the test element has its own energy source. In other embodiments, the measured data as well as the energy required for the measurement are transmitted by the transponder system in a non-contacting manner. In yet another embodiment, the polymer electronics are used for the contacts. Conductive polymers are typically insensitive even towards aggressive sweat. Moreover, by generating a voltage peak on the contact surfaces it is possible to spot-weld the contacts between the test element and measuring instrument and thus reproducibly generate a very low transition resistance.

Another embodiment of the present invention concerns a system for determining the concentration of an analyte in a body fluid which comprises an analytical test element which has an area with reagent chemistry to detect the analyte in a body fluid as well as a memory for storing electronic data. In addition, the system comprises an instrument which has an evaluation unit for evaluating the data and a display unit. The system is characterized in that at least a part of the electrical components of the system comprises polymer electronics.

The electronic data stored on the analytical test element can comprise a test strip identification, lot-specific calibration data and the measured values generated in the concentration measurement. The test strip identification e.g. lot number, strip type and the expiry date, are preferably already stored on the test element during the manufacture of the test strip and are subsequently no longer altered. Hence this could also be achieved by hard wiring. Otherwise single or multiple rewritable software memories e.g. an EPROM or EEPROM can also be used for this. According to embodiments of the present invention, a rewritable polymer electronic memory can be employed for this purpose.

A memory that can be written by a transponder system is useful to store calibration data on already packaged analytical test elements. Furthermore, it may be expedient to store the measurement signals obtained during the concentration measurement on the analytical test element before the data are transmitted to the measuring instrument. In this manner it is possible to transmit the measurements several times as required, e.g. when an error occurs in the transmission to the measurement instrument.

Furthermore, it is also possible that the transmitting module receives energy transmitted from the reading module, e.g. as soon as the analytical test element is inserted into the instrument, especially if the analytical test element does not have its own energy supply. In the case of a passive transponder system the transponder does not have its own energy supply and is thus only active while it is in contact with the reaming unit. Such transponders typically operate in the near field by magnetic field coupling, i.e. the transponder has to be moved close enough to the reading unit. When writing the transponder, the data are stored in an electrically writable memory e.g. an EPROM or an EEPROM and are permanently stored after removing the energy.

In an embodiment of the present invention, the analytical test element does not have its own source of energy. In this case the electrical energy required for the measurement and possibly also for the storage is transmitted from the instrument to the test element by means of the transponder system. This embodiment is useful for implanted devices since the residence period of the implant is then not limited by the lifespan of the power source e.g. a battery. In the case of analytical test elements which are used as disposables for a single in vitro measurement (so-called single use test strips), a potential cost reduction may be realized when the test element does not require its own energy supply.

In other embodiments, it is instead possible to integrate a temporary energy store into the test element, for example a capacitor or accumulator. This allows more flexibility within the proximity of modules to each other over time, and thus, for example, a continuously measuring system with such an energy buffer can continue to measure over a long period irrespective of whether the instrument is permanently in the vicinity of the test element.

In a further embodiment according to the present invention, the analytical test element has its own energy supply. Such a so-called active transponder may be useful when the test element can carry out several measurements. For example, an implanted test element could carry out the required or preset measurements over 24 hours and the user only needs to transfer the measurement data once daily from the test element to the instrument. In yet further embodiments, the test element has a rechargeable energy supply (accumulator, capacitance) such that the energy store can be charged as required during data transmission.

In another embodiment, the analytical test element of the system according to the present invention comprises several electrodes, e.g. more than two electrodes, which are in contact with the reagent chemistry. The electrodes are connected to one or more electronic circuits and the electronic circuits are galvanically separated, i.e. the circuits do not have a common energy source or common ground and are galvanically isolated from the outside to such an extent that the only connection is via the unavoidable liquid path of the reagent chemistry itself. Since there is an electrical contact at only one site, it should not be possible for any parasitic leakage current path to build up which could falsify the measurement. Typicallyy, in order to achieve a galvanic separation, each circuit should have its own power supply. This would be very expensive, however. According to embodiments of the present invention, the galvanic decoupling is achieved instead by the transponder system. In such embodiments, all circuits on the analytical test element have a transponder and are separated galvanically from one another. A common reading module or individual reading module for each transponder transmits the energy to the circuits. In this case, the reading module can be located in the instrument or also on the analytical test element. In the latter case energy can be transferred from the reading module which is located on the test strip to the instrument either by electrical contacts or by another transponder system consisting of a common transponder or again consisting of several transponders.

Simple electrochemical systems typically consist of two to three electrodes. So-called potentiostats with 3 electrodes (working, counter and reference electrode) are frequently used. In this regard, a parasitic resistance from the counter electrode to the output of the potentiostat is particularly critical since this resistance has a direct effect on the signal amplification. It is therefore useful to have the entire potentiostat except for the electrodes substantially sealed by an insulating layer. In this embodiment the transponder typically processes and stores no digital information but rather processes the analog signal current and transmits it to the reading module. The functions necessary for the measuring process are integrated into the transponder, such as permanent supply of the working electrode with a potential (typically a few hundred mV, preferably—350 mV). In this case the transponder system is designed such that the required energy is provided by the instrument at suitable refresh intervals and is temporarily stored.

In the case of a potentiostat which is designed as an implant or partial implant, e.g. for the continuous measurement of an analyte, the electrical system can be sealed or encapsulated by the use of transponder technology according to embodiments of the present invention, and nevertheless information and energy can be transmitted.

An embodiment according to the present invention concerns implanted analytical test elements. The use of transponder technology enables a test element to be implanted in the body and to be operated from the outside without transcutaneous connections. Leads through the skin reduce the wearing comfort, e.g. when showering, and involve the inherent risk of an infection. Thus, for example, an analytical test element for the continuous measurement of blood glucose can be inserted into the subcutaneous adipose tissue in the abdominal region and the instrument can be held outside on the skin either temporarily in order to carry out a measurement or permanently by a belt or a brace, such as in the case of continuous measurements of the analyte in the one minute range. In both cases the instrument can be removed at least briefly e.g. for showering. Even in the case of partially implanted analytical test elements, one end of which is for example integrated into a brace whereas the other, typically lancet-shaped end is inserted into the abdominal wall, the relatively large and heavy instrument for the measurements can be positioned near to the test element and if necessary simply removed. Since the partial implant has no open electrical contacts, it is also in this case considerably less sensitive to environmental influences. Moreover, the instrument can also be worn over the clothes especially when it is also comprises a display unit. Irrespective of whether it is equipped with or without a display unit, the instrument can store a considerable amount of the received data, for example several hundred measurements.

A method for transmitting data with the transponder system according to the present invention comprises converting the signals which are typically direct current or direct voltage signals into a frequency and to modulate a carrier frequency onto it which is used for example for energy transfer.

One alternatives embodiment of the present invention describes the use of different carrier frequencies. These can be used to differentiate between the transponder systems. Especially when several transponders are addressed simultaneously for example when several parallel transponders are present on one analytical test element or when writing several test strips which are in one package, it may be useful to individually address each transponder. Each carrier frequency can be treated individually and crosstalk or other interferences can be avoided, for example by using narrow band filters.

Another feature of embodiments of the present invention is that the signals transmitted by the transponder system can comprise not only digital data, e.g. calibration data, but also analog signals, e.g. the measured values obtained during the measurement of the analyte concentration. Current transponder systems are typically used only to transmit digital data. DE 103 22 167 for example describes the use of transponders for the logistical backtracking of reusable load carriers; U.S. Pat. No. 6,579,498 discloses a transponder-assisted transmission of digital data in an implanted blood glucose sensor. In the above-mentioned publication of J. Black the feasibility of a wireless transmission of analog data for glucose measurement is for example demonstrated.

Typically the calibration and identification data of the analytical test element are present as digital data and the measured signals obtained in the measurement of the concentration of an analyte are in the form of analog data. In the application of transponder technology according to embodiments of the present invention, the digital data can be transmitted by the above-mentioned amplitude modulation. The analog data are either digitized before transmission or they are transmitted as analogue signals by for example also using amplitude modulation.

The calibration and identification data which are stored on the analytical test element can be either stored in an electronic memory such as one made of polymer electronics or they can be coded in a magnetic strip or barcode which is located on the test strip. The measurement signals are either stored on an electronic data memory before they are transmitted to the instrument e.g. by a transponder system, or they are directly transmitted to the instrument without temporary storage. The electronic memory on the analytical test element can be a non-transient memory, such as the memory or memory area in which the calibration and identification data are stored.

In an embodiment of the present invention, the analytical test element comprises a memory for storing electronic data wherein the memory is also writable when the analytical test element is in a package. For example, the test strips may be packaged in a container (single test magazine or tape magazine) and subsequently the calibration data transmitted from the reading module located on the outside, through the package to the transponder located on the test element on the inside, and are stored there. In this case the package is designed such that a wireless transmission of the data is possible. For example, the packaging material may comprise plastic or cardboard which is configured to be almost completely permeable to the transmission.

In another embodiment according to the present invention the analytical lest element has no electrical contacts with the instrument by which data or electrical energy can be transmitted between the test element and the instrument. Instead, all data and optionally the measurement energy are transmitted by the transponder system.

For example, the electric circuit on the analytical test element, such as the transponder antenna or the conductor paths and contacts, at least partially made of polymer electronics but the transponder itself is in the form of, e.g., a silicon chip. The higher manufacturing costs of a silicon chip may be acceptable for complex analytical test elements which can for example carry out several measurements. This embodiment can be useful when the transponder is not directly located on the analytical test element but on a package for one or more test elements. In this alternative embodiment the system additionally comprises such a package which can in particular be a container or a magazine for a plurality of test elements e.g. a drum. In addition, it is possible to implement a so-called test counter on the package which stores the number of tests carried out or still to be carried out with this container in the memory on the container. In this manner the instrument can at any time inquire how many unused test elements are still the package. If this information is only stored in the instrument, malfunctions, may occur, for example when a container that has been started is removed from the instrument and replaced by another partially used or new container. Of course, an indicator showing whether the test element has been already used or not can also be stored on the test element itself.

Another embodiment of the present invention concerns a system which comprises an analytical test element which has an area with reagent chemistry for detecting the analyte wherein at least a part of the electrical components on the test element comprises polymer electronics, and a package in which one or more analytical test elements are packaged wherein the package has a memory for storing electronic data and a transmitting module for the wireless transmission of data. The system additionally comprises an instrument which has an evaluation unit for evaluating the data and a reading module for the wireless transmission of data.

In such an embodiment, the test strips can be packaged in a container (drum, magazine). The calibration and identification data in this case can be stored on the container and not on the test elements. The container, e.g. a drum containing analytical test elements which is similar to that used in the Accu-Chek Compact, is inserted into the instrument and the transponder on the container transmits the data to the reading module in the instrument. In this embodiment only one transmitting module can be provided for several test strips, especially when the measurement signals can be processed without a transponder (e.g. in the case of photo-optical test elements).

According to another embodiment according to the present invention, the analytical test element does not have its own energy supply. Lot number, strip type, expiry date and calibration data are for example stored on the test element. The test element is removed from the package by the user or automatically by the instrument and for example moved into a holder in the instrument. The positioning of the test element in the holder ensures a correct position of the transmitting and reading modules. In particular the holder ensures that the analytical test element is positioned in the transmitting and receiving range of the reading module. The transmitting and receiving range describes the range within which electronic data can be exchanged in a wireless manner between the reading module and transmitting module. The extent of this range is defined in particular by the dimensions of the transponder coils, the energy and frequency of the transmitted electromagnetic waves and any shielding that may be present e.g. by metal parts. For example, the holder can be designed such that the transponder modules are brought very close together, typically to a distance of 0.1 to 3 mm. Due to the small distance which has to be bridged, the transponder coils can be very small and only a small amount of energy should be required for a wireless transmission, for example in the range of 0.1 to 10 mJ. A low energy requirement is useful for battery operated instruments. Furthermore, the transmitting and receiving area can be spatially considerably narrowed down to ensure that only the inserted test element is addressed and not additionally other test elements that are in the vicinity. Alternatively the transmitting and receiving area can also be designed such that the analytical test element can be positioned with or without a holder, for example right next to or on the instrument for wireless data transmission. Furthermore, the holder for inserting the analytical test element into the transmitting and receiving area can be located in a package for several test elements and the package is appropriately positioned relative to the instrument for example by a holder for the package on the instrument or by a holder for the instrument on the package.

In another embodiment the transmitting module is not on the test element but rather on a package which contains one or more test elements and a holder positions the package in the instrument such that the transmitting and reading module are brought very close together so that the transmitting module of the package is in the transmitting and receiving range of the reading module.

Another embodiment of the present invention concerns an analytical test element which has an area with reagent chemistry for detecting an analyte wherein a transmitting module and a reading module are located on the analytical test element and data are transmitted in a wireless manner between these two modules within the test strip. Furthermore, electrical energy can also be transmitted in addition to the data. At least some of the electrical components on such an analytical test element can comprise polymer electronics. Such an analytical test element can in addition also transmit data or data and energy to the instrument in a wireless manner, e.g. by means of a second transponder system with a transmitting module on a test strip and reading module in the instrument. Of course the data which are transmitted within the test strip using a transponder system can be digital as well as analog data. For example, such an internal transponder system on the test strip can be used to galvanically decouple the electric circuits on an electrochemical test strip wherein energy is transmitted from the instrument to the detection area and the measurement signals, e.g. as analog voltage or current values, are in turn transmitted from the detection area to the instrument.

In the embodiments according to the present invention, it is possible to use an electrochemical as well as a photo-optical measuring procedure for the analytical determination. For example, when the measuring unit is on the test strip in the case of a photo-optical test strip, the electrical measurement signals are to be generated on the test strip in a similar manner as for an electrochemical test strip, and transferred to the instrument.

For example a light beam can be guided from the instrument onto the detection area and a photoelement located on the test strip e.g. a solar cell made of polymer electronics receives the optical measurement signal and converts it into an electrical signal. This signal can then be transmitted in a non-contact manner by the transponder system to the instrument.

The methods known in the prior art are used for the sensory detection of the analyte and in particular of blood glucose. Photo-optical and electrochemical methods are useful in this regard. Photo-optical measuring procedures are for example reflection photometry, absorption measurement or fluorescence measurement. Electrochemical methods are for example potentiometry, amperometry, voltammetry and coulometry.

Another aspect of the present invention is a process for producing an analytical test element which has an area with reagent chemistry for detecting an analyte in a body fluid, a memory for storing electronic data and a transmitting module for the wireless transmission of data, wherein the production comprises the steps of: storing a lot identification on the analytical element; packaging the analytical test element; and storing calibration data on the packaged analytical test element.

Another aspect of the present invention is a process for producing an analytical test element which has an area with reagent chemistry for detecting an analyte in a body fluid, wherein the production comprises the steps of: storing a lot identification on a package which has a memory for storing electronic data and a transmitting module for the wireless transmission of data; packaging the analytical test element in the package; and storing calibration data on the package.

Another aspect of the present invention is a method for determining the concentration of an analyte in a body fluid which comprises the steps of: inserting an analytical test element which has an area with reagent chemistry for detecting an analyte in a body fluid and a memory for storing electronic data and a transmitting module for the wireless transmission of the data, into an instrument which comprises an evaluation unit for evaluating the data and a reading module for the wireless transmission of the data; applying the body fluid to the analytical test element, wirelessly transmit the data from the analytical test element to the instrument, and evaluating the data in the evaluation unit of the instrument.

Another aspect of the present invention is a method for determining the concentration of an analyte in a body fluid which comprises the steps of: inserting a package in which one or more analytical test elements with reagent chemistry for detecting an analyte in a body fluid are packaged, the package having a memory for storing electronic data and a transmitting module for the wirelessly transmitting data; providing an analytical test element from the package; applying the body fluid to the analytical test element; wireless transmission of data from the package to an instrument which comprises an evaluation unit for evaluating data and a reading module for the wireless transmission of data; and evaluating the data in the evaluation unit of the instrument.

Lot-specific calibration data can be stored on the test strip. In that case, the test strip is inserted into the appropriate holder in the instrument by the user for example by hand or the test strip storage container has a removal device which transports the strips from the storage container into the instrument. The instrument automatically switches on as soon as the test strip is inserted and is ready for measurement after a short self test. Subsequently the user applies the sample of body fluid to be measured. The sample reacts with the reagent chemistry on the test strip and thus generates a measurement signal. In the case of photo-optical systems this can for example be a change in color and in the case of electrochemical systems a current signal is for example generated.

The color change is converted by the optical measuring system into an electrical signal. The optics are typically integrated into the instrument but can, however, also be located on the test strip especially when the optical system at least partially comprises polymer electronics. The calibration data are transmitted in a wireless manner from the test strip to the instrument with the aid of the transponder system or if the optical system is on the test strip, energy is firstly additionally transmitted from the instrument to the test strip to drive the optical system and after the measurement the measurement signals are transmitted from the test strip to the instrument. The measurement signals are evaluated in the evaluation unit taking into account the lot-specific calibration data. The instrument typically comprises a display unit, e.g. an LCD display which shows the measurements to the user.

In an alternative embodiment one or preferably a plurality of test strips are arranged in a package, e.g. a cartridge. The lot-specific calibration data are stored on the package and the transponder is also located in the package. The package is inserted into the instrument by the user. The instrument is switched on for operation and transports, e.g. automatically a test strip into a position in which the user can apply the sample. Subsequently the sample is applied and a photo-optical or electro-chemical measurement is carried out as described above. For a photo-optical test strip, the optical measuring system is located in the instrument. The calibration data are transmitted by the transponder on the package to the instrument in a wireless manner before or after the measurement, while the optical measurement signals are received by the optical system in the instrument and evaluated in the evaluation unit taking into account the calibration data and displayed in a display unit. In the case of an electrochemical test strip, calibration data are also transmitted by the transponder on the package to the instrument in a wireless manner and for example the electrical measurement signals are transmitted via electrical contacts from the test strip to the instrument by means of which the energy required for generating the measurement signal is also fed in.

These and other features and advantages of the present invention will be more fully understood from the following detailed description of the present invention taken together with the accompanying claims. It is noted that the scope of the claims is definitely by the recitations therein and not by the specific discussion of the features and advantages set forth in the present description.

BRIEF DESCRIPTION OF THE DRAWINGS

The present invention is further elucidated by the following figures.

The following detailed description of the embodiments of the present invention can be best understood when read in conjunction with the following drawings, where like structure is indicated with like reference numerals and in which:

FIG. 1 shows a perspective view of an embodiment of an analytical test element with a transponder system.

FIG. 2 shows a schematic view of an analytical test element according to an embodiment of the present invention inserted into an instrument.

FIG. 3 shows a sectional view of the use of a conductive polymer substrate as a data memory.

FIG. 4 shows the transmission of data on several analytical test elements using the transponder system according to embodiments of the present invention.

FIG. 5 illustrates an embodiment of a system comprising several galvanically separated circuits.

FIG. 6 shows a schematic block diagram of an embodiment of a system comprising several galvanically separated circuits.

FIG. 7 shows an embodiment of a multielectrode system with transponder.

FIG. 8 shows an embodiment of a partially implanted analytical test element.

FIG. 9 shows an embodiment of an implanted analytical test element.

FIG. 10 shows a basic circuit diagram of an embodiment of a potentiostat transponder.

FIG. 11 shows a perspective view of an embodiment of an electrochemical test strip with a transponder made of polymer electronics.

FIG. 12 shows a sectional view of the test strip of FIG. 11 inserted into an instrument.

FIG. 13 shows a perspective view of an embodiment of a photo-optical test strip with a transponder made of polymer electronics.

FIG. 14 shows a sectional view of the test strip from FIG. 13 inserted into an instrument.

FIG. 15 shows a perspective view of an embodiment of a test element with several potentiostat sensor systems.

FIG. 16 shows the test element of FIG. 15 inserted into an instrument.

FIGS. 17 and 18 show alternative embodiments of a partially implantable analytical test element.

FIGS. 19 to 21 show alternative embodiments for data transmission on packaged test strips.

FIGS. 22 and 23 show alternative embodiments of a writing/reading memory made of polymer electronics.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the present invention may be more readily understood reference is made to the following examples, which are intended to illustrate the present invention, but not limit the scope thereof.

DETAILED DESCRIPTION

The following description of the preferred embodiment is merely exemplary in nature and is in no way intended to limit the present invention or its application or uses.

Figure 1:
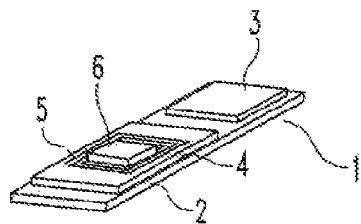
FIGS. 1 to 23 show schematic diagrams for specific embodiments of the present invention.

An analytical test element 1 is shown in FIG. 1 which consists of a substrate 2 on which a detection area 3 for detecting an analyte in a body fluid and a transmitting module which comprises the transponder substrate 4, in or on which the transponder antenna 5 and the transponder electronics 6 are located, which are manufactured as polymer electronics.

Figure 2:
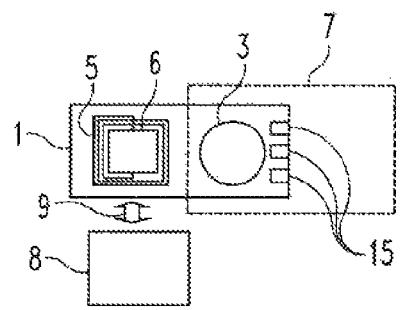

FIG. 2 shows a schematic drawing of an analytical test element 1 which is inserted into an instrument 7. The identification and calibration data of the test strip are stored in the transponder electronics 6 and are transmitted via the transponder antenna 5 to the reading module 8 which is also situated in the instrument 7. The wireless data transmission is indicated by the arrow 9. The measurement signals determined in the detection area 3 are passed onto the instrument 7 via the electrical contacts 15. The test strip shown here can be suitable for an electro-chemical and for a photo-optical measurement. In the case of a photo-optical test element either the contacts 15 are omitted and the optical evaluation system is in the instrument 7, or the optical evaluation system is at least partially integrated on the test strip such that the optical measurement signals on the test element are converted into electrical quantities and the electrical signals are passed onto the instrument via the contacts 15.

Figure 3:
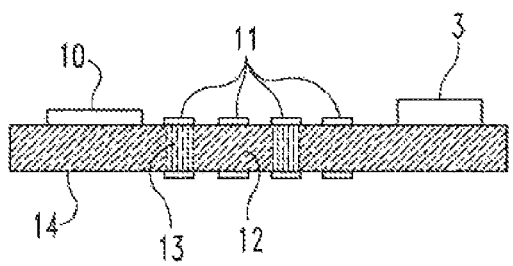

Use of a conductive polymer substrate 14 as a binary memory for electronic data is shown schematically in FIG. 3. The control electronics 10 controls the electrode matrix 11 such that firstly high-resistance zones 12 become low-resistance zones 13 in a spot-wise manner.

Figure 4:
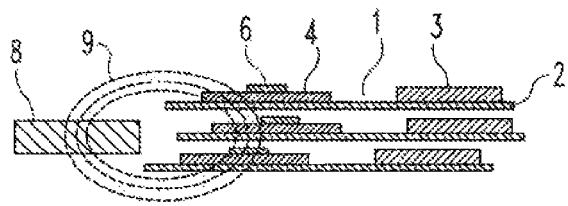

FIG. 4 shows the wireless transmission of data 9 between a reading module 8 and several analytical test elements 1. The transmitting modules on the test element are in this case represented by the transponder substrate 4 and the transponder electronics 6. This application can for example be used in the test element production. In this case the test strips 1 are packaged in a package, e.g. a cartridge which does not impede the electromagnetic field and a special reading module 8 in the production firstly reads the test strip identification from the test elements in order to read the lot numbers, it then transmits the lot-specific calibration data and finally checks by means of a new interrogation whether the data transmission was correct. In a second application of the setup shown here, the test elements 1 are in a container in the instrument or in close proximity to the instrument and the reading module 8 which is located in the instrument reads the data from the test element. These data comprise, e.g., the type of strip, expiry date and calibration data. Furthermore, it is also possible that used test elements are placed back in the container after the measurement. The use is for example stored on the test element e.g. together with the measured values and reported to the reading module, or directly transmitted to the reading module and stored there for example together with the measured values, or a test element for which a measured value has been stored on the test element or in the instrument, is automatically regarded as having been used.

Figure 5:
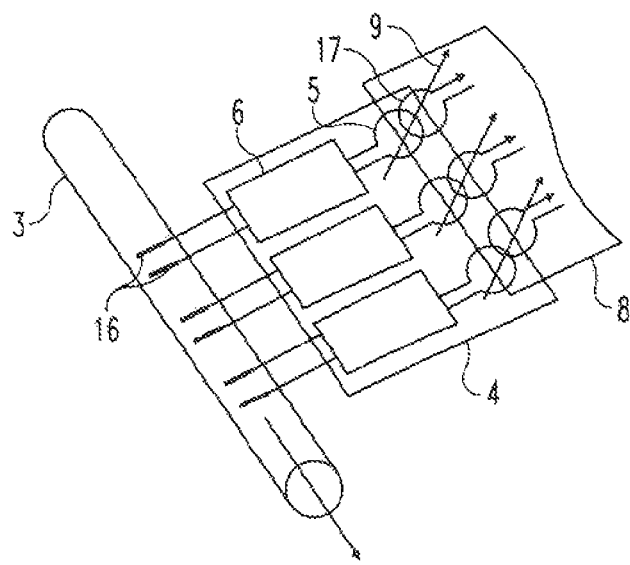

FIG. 5 shows a basic diagram of a system with galvanically separated circuits. Several electrical circuits consisting of transponder antenna 5, transponder electronics 6 and measuring electrodes 16 extending into the electrochemical detection area 3 are located on the transponder substrate 4. The measurements signals are received by an equal number of antennae 17 arranged in parallel in the reading module 8.

Figure 6:
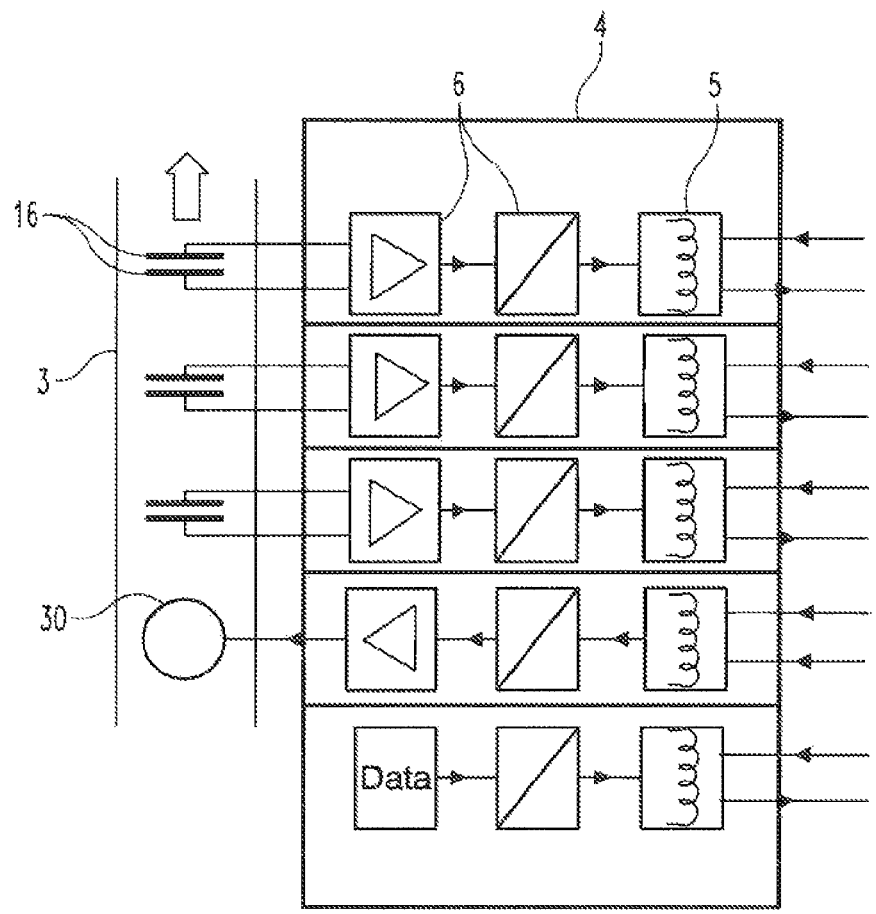

FIG. 6 shows a simplified block diagram of the example shown in FIG. 5 where it is also possible to transmit and/or receive signals from further modules 30 e.g. an electrochemical flow sensor.

Figure 7:
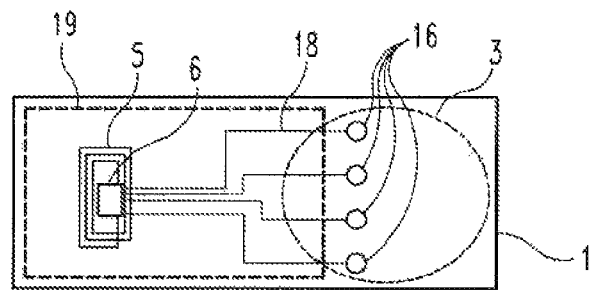

FIG. 7 shows a complex multielectrode system as a potentiostat transponder for the electrochemical measurement of for example blood glucose and blood coagulation using electrical supply lines 18 which extend from the transponder electronics and transponder antenna 6 and 5 respectively to the measuring electrodes 16 in the detection area 3. A cover layer 19 ensures a hermetic separation of the transponder system.

Figure 8:
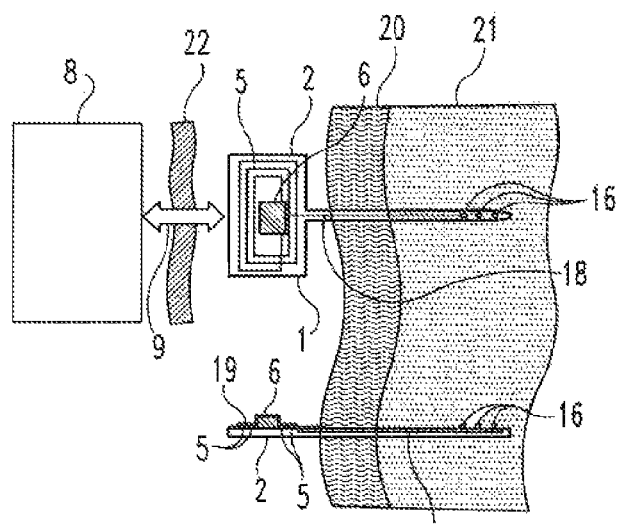

FIG. 8 shows a partially implantable lancet-like test element 1 having a potentiostat transponder which is preferably used for a continuous glucose measurement. In this case the glucose concentration is determined regularly, the data are stored in the transponder and the signals are always transmitted to the instrument when the reading module 8 is in the vicinity. Thus the user can remove the instrument for brief periods e.g. to change his clothes or shower without problems. The test element 1 consists of a relatively stiff substrate 2 which is pointed at one end and on the tip of which the measuring electrodes 16 are situated. Electrical conductor paths 18 lead from the electrodes 16 to the other transmitting module located outside the body consisting of transponder electronics and transponder antenna 6 and 5 respectively. The entire test element 1 is encapsulated in a water-tight manner with a cover layer 19 and only the measuring electrodes 16 have, of necessity, contacts that are open towards the outside. There may for example be a plaster 22 over the test element 1 and the reading module 18 can be worn comfortably above the clothing 22.

Figure 9:
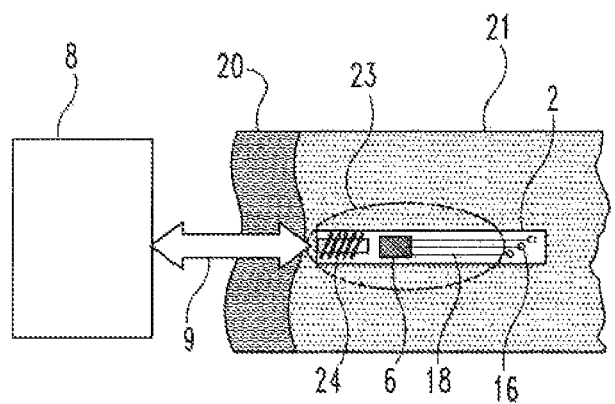

FIG. 9 shows a potentiostat test element 1 similar to the example shown in FIG. 8 as a (fully) implanted version. The entire electronics except for the measuring electrodes 16, is sealed or encapsulated in a glass or polymer capsule 23. In order to achieve higher penetration depths into the tissue layers, one preferably uses low frequency transponders in the range of 125 kHz. In order to achieve small antenna coils that are suitable for this, they are equipped with rod ferrite cores 24.

Figure 10:
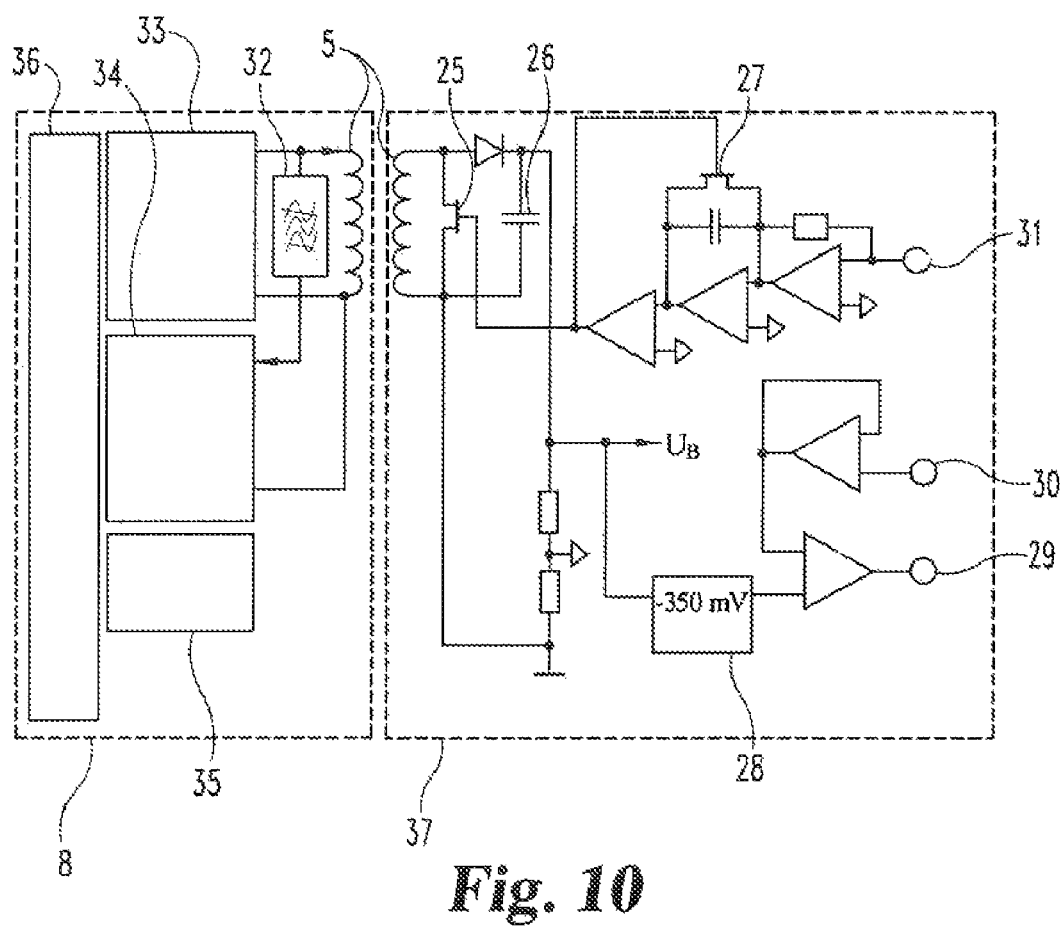

FIG. 10 describes a basic circuit for an exemplary potentiostat transponder. The transponder electronics comprises among others a load modulator 25, an energy store 26 e.g. in the form of a capacitance and a voltage/frequency converter 27. The resting potential 28 is permanently applied to the working electrode 29, 30 and 31 denote the reference and counter electrode respectively. The reading module has among others a band pass filter 32, energy transmitter and writing unit 33, reading unit 34, memory 35 and control unit 36.

Figure 11:
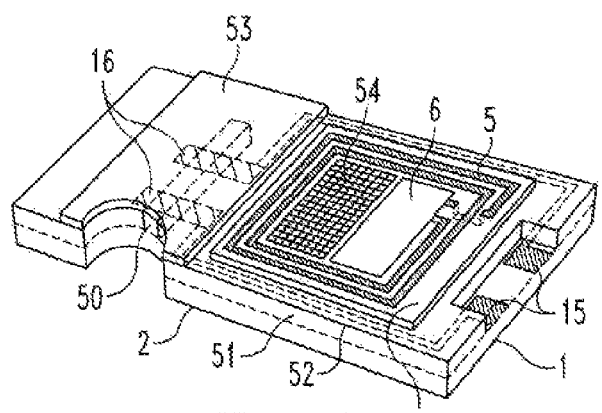

FIG. 11 shows an analytical test element 1 with a transponder made of polymer electronics which operates according to an electrochemical measuring procedure. A spacing foil 51 is located on the substrate 2 and forms a blood capillary 50 between the substrate 2 and cover foil 52 into which the measuring electrodes 16 for the electrochemical measurement extend. The transponder antenna 5, the transponder electronics 6 and the transponder memory 54 comprising polymer electronics are in or on the transponder foil 4. In this case the transponder is used to transmit test strip identification and calibration data. The measurement signals are transmitted via the sensor contacts 15.

Figure 12:
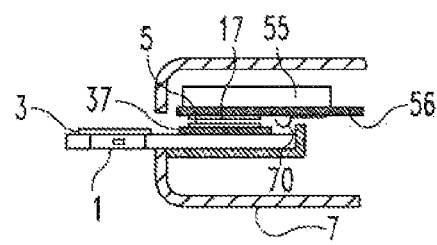

Insertion of the test strip 1 from FIG. 11 into an instrument positions the transmitting module 37 and in particular the transponder antenna 5 close to the reading module 55 and in particular close to the reading module antenna 17 (see FIG. 12). In this case the reading module 55 is located on the electronic printed circuit board 56 of the instrument 7 as are the instrument contacts 70 which contact the sensor contacts 15 on the test strip 1.

Figure 13:
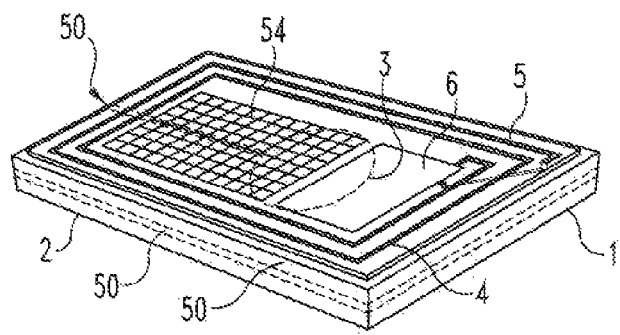

In the test element 1 from FIG. 13 the detection area 3 which is filled by the blood capillary 50 is located under the polymer electronic transponder module consisting of transponder substrate 4, transponder antenna 5, transponder electronics 6 and transponder memory 54. The blood capillary 50 is formed by the spacing foil 51 between the substrate 2 and cover foil 52.

Figure 14:
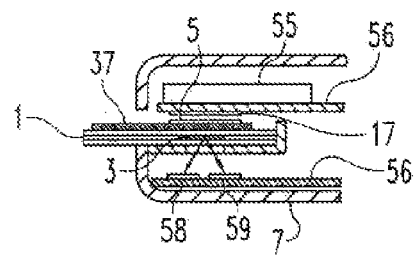

When the test element 1 from FIG. 13 is inserted into an instrument 7, the transponder antenna 5 and reading module antenna 17 are very close above one another and thus ensure an easy data transmission over a short distance (see FIG. 14). The transponder module 37 is on the upper side of the test strip the photo-metric detection area 3 is illuminated from the underside by the illumination 58 and read by the optical reader 59. Printed boards 56 lying above and below are fitted with the reading module 55 and the optical modules 58 and 59 respectively.

Figure 15:
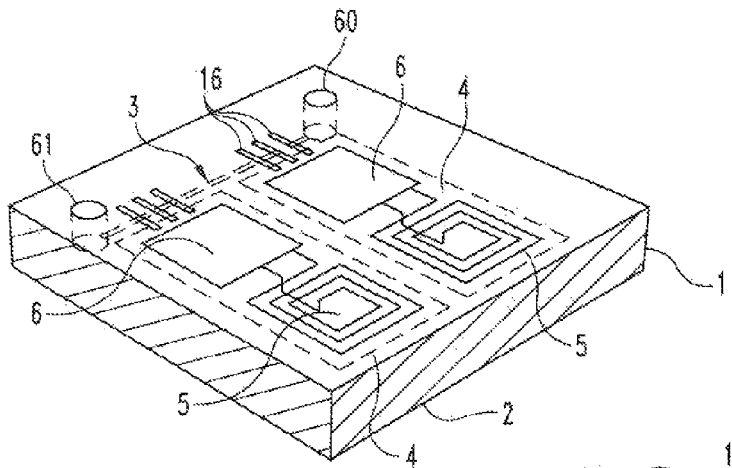

The test element 1 in FIG. 15 has a detection area 3 in the form of a liquid channel through which the sample flows from the inlet 60 to the outlet 61 e.g. for continuous blood glucose measurement. Three measuring electrodes 16 of a potentiostat extend into the liquid channel. A polymer electronic transponder antenna 5 and the transponder electronics 6 which is composed of polymer electronics or (at least partially) silicon chips are located on the transponder substrate 4. In addition to the first potentiostat sensor system there is another parallel system of identical construction where both systems are galvanically separated from one another.

Figure 16:
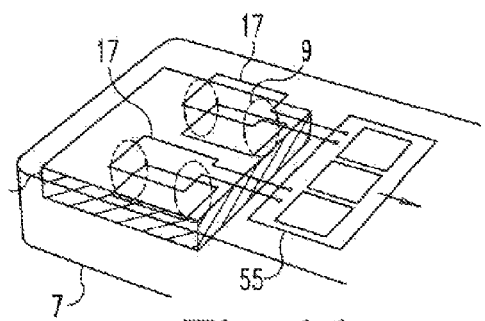

When inserted into an instrument 7 the parallel transponder antennae 5 on the test element 1 are aligned with the corresponding reading module antennae 17 which pass the data onto the reading module electronics 55 for a wireless data transmission 9 (see FIG. 16).

Figure 17:
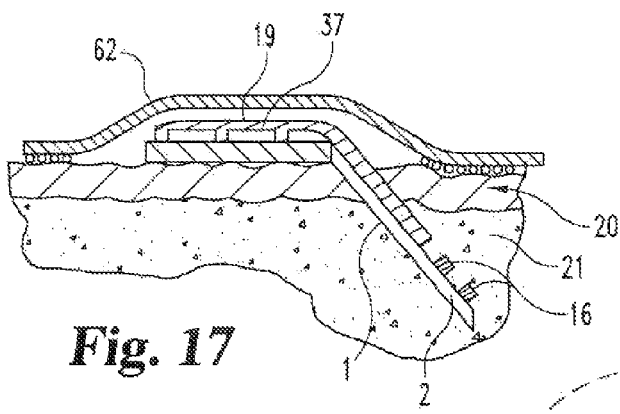
Figure 18:
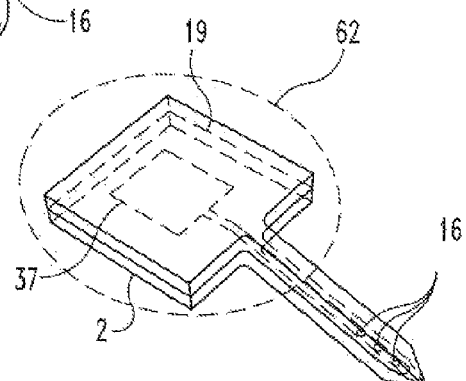

Another example of a continuously measuring analytical test element 1 is shown in FIGS. 17 and 18. The substrate 2 has a needle-like end which is inserted through the skin 20 into the tissue 21 such that the measuring electrodes 16 can measure directly in the tissue 21. The potentiostat electronics and the transponder module 37 as polymer electronics or a silicon chip are situated on the flat extracorporeal part of the substrate 2. A cover layer 19 encapsulates the electronics with the exception of the measuring electrodes. A brace 62 attaches the test element 1 to the skin.

Figure 19:
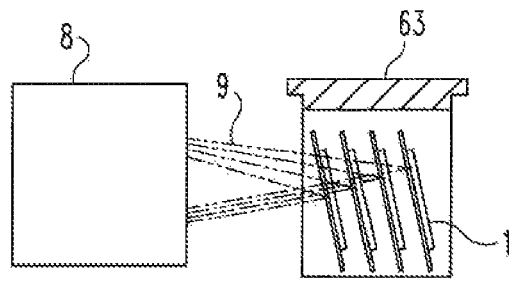
Figure 20:
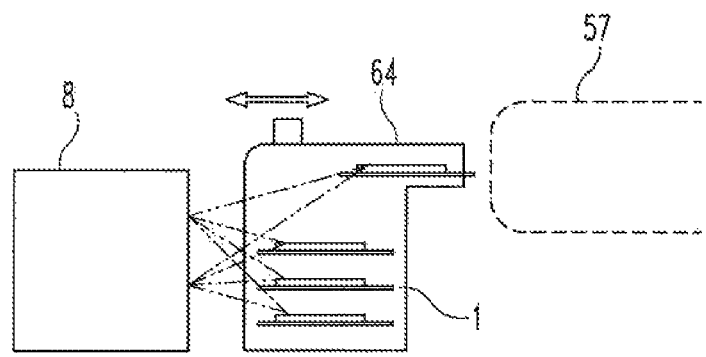
Figure 21:
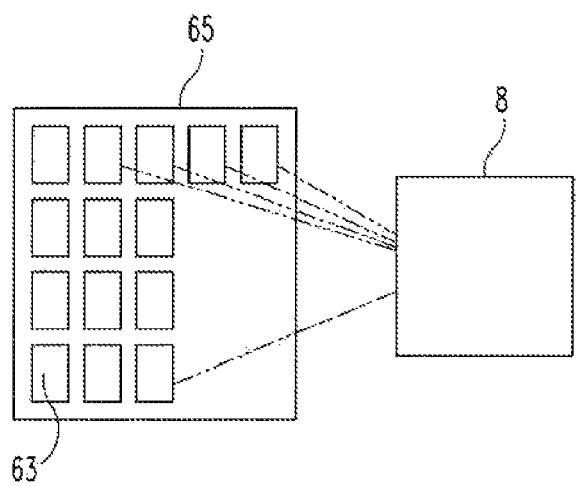

FIGS. 19 to 21 show examples for data programming in production and logistics. In FIGS. 19 and 20 a reading module 8 writes lot-specific calibration data onto test strips 1 during the production where the test strips are already packaged in a drum 63 or a magazine 64. In FIG. 21 several test strip cans 63 are combined in a cardboard box 65 to make a package and are then written by a reading module 8 in the production or in the logistic chain. It is also possible to hard-wire data (e.g. lot numbers or serial numbers of the test strips) during the manufacture of the polymer electronic transponder. The data then do not have to be read additionally onto the transponder but can also not be subsequently changed.

Figure 22:
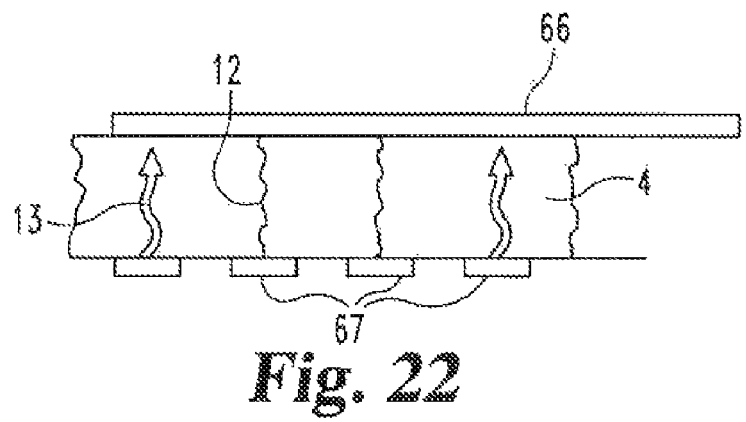
Figure 23:
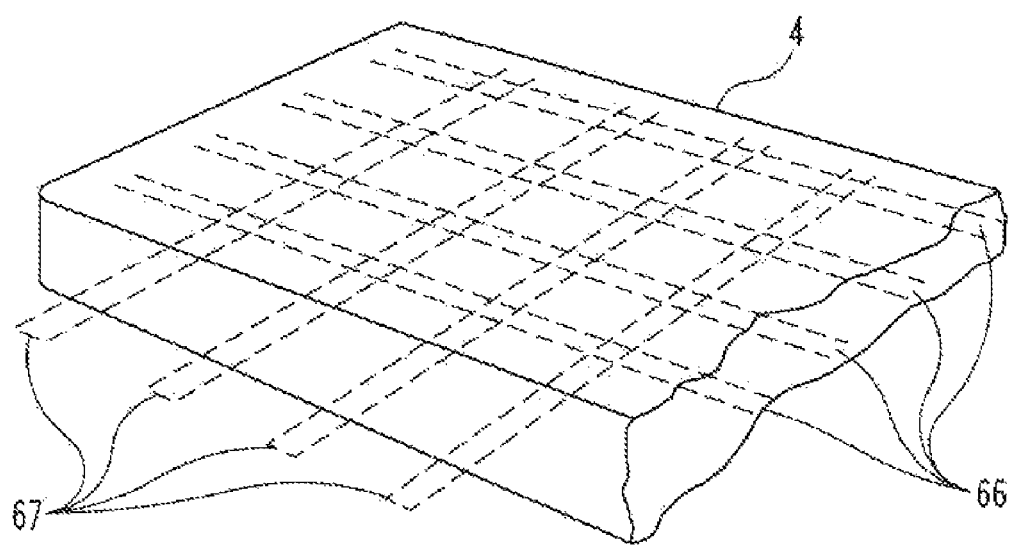

FIGS. 22 and 23 show a writing/reading memory made of polymer electronics as is for example used for a transponder memory 54. The polymer substrate 4 e.g. made of PDOT (polyethylene dioxythiophene) has line leads 66 on the upper side and column leads 67 on the underside. By applying a voltage to a certain line lead 66 and a certain column lead 67, the polymer 4 changes its electrical conductivity at the crossing point from high-resistance 12 to low-resistance 13. The effect can be reversed by reversing the polarity of the voltage, when the voltage is removed the last resistance value is retained. In this manner a binary data memory is obtained. 10 lines and 10 columns are for example sufficient to store the calibration data of a blood glucose test strip. The data are read out again by measuring the resistances between defined column and line leads.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A system for determining the concentration of an analyte in a body fluid comprising:
    an analytical test element having an area with reagent chemistry for detecting the analyte in a body fluid by generating a measurement signal from the reaction of the analyte with the reagent chemistry;
    an instrument separate from said analytical test element, said instrument comprising an evaluation unit configured to evaluate the measurement signal and determine the concentration of the analyte in the body fluid, the analytical test element and the instrument being operatively connected in either a contacting or non-contacting manner;
wherein said analytical test element comprises electrical components at least in part comprising polymer electronics, the electrical components on the analytical test element comprising at least two electrodes in contact with the reagent chemistry and a plurality of galvanically separated electronic circuits and a plurality of parallel transmitting modules configured for wireless transmission of data or data and energy, the instrument further comprising a plurality of parallel reading modules corresponding to said plurality of parallel transmitting modules configured for wireless reception of data or data and energy.

2. A system according to one of the claim 1, wherein the analytical test element has a memory for storing data.

3. A system according to claim 1, wherein data which are transmitted in a wireless manner between the transmitting module on the analytical test element and the reading module on the instrument at least partially comprise analog data.

4. A system according to claim 1, wherein the analytical test element further comprises a memory for storing data, wherein the memory is writable when the analytical test element is located in a package.

5. A system according to claim 1, wherein a transmitting module and a reading module are located on the analytical test element and data or data and energy are transmitted in a wireless manner within the analytical test element between the modules.

6. A system according to claim 1, wherein the instrument comprises a holder for positioning the analytical test element.

* * * * *